(12) United States Patent
Fraser et al.

(10) Patent No.: US 7,112,222 B2
(45) Date of Patent: Sep. 26, 2006

(54) ANTERIOR LUMBAR INTERBODY FUSION CAGE WITH LOCKING PLATE

(75) Inventors: Robert Fraser, Adelaide (AU); John D. Malone, Cumberland, RI (US); Hassan A. Serhan, S. Easton, MA (US); Richard C. Techiera, Avon, MA (US)

(73) Assignee: Depuy Spine, Inc., Raynham, MA (US)

( * ) Notice: Subject to any disclaimer, the term of this patent is extended or adjusted under 35 U.S.C. 154(b) by 317 days.

(21) Appl. No.: 10/403,930

(22) Filed: Mar. 31, 2003

(65) Prior Publication Data
US 2004/0193269 A1   Sep. 30, 2004

(51) Int. Cl.
*A61F 2/44* (2006.01)

(52) U.S. Cl. ...................... 623/17.11; 606/61

(58) Field of Classification Search ............... 606/61, 606/69–71; 623/17.11, 17.15, 17.16
See application file for complete search history.

(56) References Cited

U.S. PATENT DOCUMENTS

| | | |
|---|---|---|
| 4,599,086 A | 7/1986 | Doty |
| 4,743,256 A | 5/1988 | Brantigan |
| 4,834,757 A | 5/1989 | Brantigan |
| 4,878,915 A | 11/1989 | Brantigan |
| 5,192,327 A | 3/1993 | Brantigan |
| 5,306,309 A | 4/1994 | Wagner et al. |
| 5,397,364 A | 3/1995 | Kozak et al. |
| 5,425,772 A | 6/1995 | Brantigan |
| 5,443,515 A | 8/1995 | Cohen et al. |
| 5,522,899 A | 6/1996 | Michelson |
| 5,607,424 A | 3/1997 | Tropiano |
| 5,658,335 A | 8/1997 | Allen |
| 5,658,337 A | 8/1997 | Kohrs et al. |
| 5,713,899 A | 2/1998 | Marnay et al. |
| 5,716,415 A | 2/1998 | Steffee |
| 5,755,798 A | 5/1998 | Papavero et al. |
| 5,766,252 A | 6/1998 | Henry et al. |
| 5,776,199 A | 7/1998 | Michelson |
| 5,782,832 A | 7/1998 | Larsen et al. |
| 5,800,550 A | 9/1998 | Sertich |
| 5,824,094 A | 10/1998 | Serhan et al. |
| 5,861,041 A | 1/1999 | Tienboon |
| 5,865,845 A | 2/1999 | Thalgott |
| 5,888,227 A | 3/1999 | Cottle |
| 5,888,228 A | 3/1999 | Knothe et al. |
| 5,904,683 A * | 5/1999 | Pohndorf et al. ............. 606/61 |
| 5,954,722 A * | 9/1999 | Bono ........................... 606/61 |
| 5,961,554 A | 10/1999 | Janson et al. |
| 5,964,807 A | 10/1999 | Gan et al. |

(Continued)

FOREIGN PATENT DOCUMENTS

DE          29511146          6/1995

(Continued)

*Primary Examiner*—Corrine McDermott
*Assistant Examiner*—Thomas J. Sweet
(74) *Attorney, Agent, or Firm*—Nutter, McClennen & Fish LLP (57) ABSTRACT

A spinal fixation assembly is provided including a fusion cage with posterior, anterior, superior, and inferior faces, and a plate having at least one aperture for receiving a bone screw and having a mating element adapted to slidably engage and mate to the anterior face of the fusion cage. The cage is adapted to be positioned between adjacent vertebrae, and the plate is effective to mate to the cage and to receive one or more bone screws to fasten the plate and secure the fusion cage to the adjacent vertebrae.

24 Claims, 5 Drawing Sheets

U.S. PATENT DOCUMENTS

| | | |
|---|---|---|
| 5,976,187 A | 11/1999 | Richelsoph |
| 6,019,793 A | 2/2000 | Perren et al. |
| 6,045,579 A | 4/2000 | Hochshuler et al. |
| 6,080,193 A | 6/2000 | Hochshuler et al. |
| 6,093,205 A | 7/2000 | McLeod et al. |
| 6,096,080 A | 8/2000 | Nicholson et al. |
| 6,113,638 A | 9/2000 | Williams et al. |
| 6,120,503 A | 9/2000 | Michelson |
| 6,156,037 A | 12/2000 | LeHuec et al. |
| 6,168,596 B1 | 1/2001 | Wellisz |
| 6,176,882 B1 | 1/2001 | Biedermann et al. |
| 6,231,610 B1 | 5/2001 | Geisler |
| 6,235,033 B1 | 5/2001 | Brace et al. |
| 6,235,059 B1 * | 5/2001 | Benezech et al. ........ 623/17.16 |
| 6,290,703 B1 | 9/2001 | Ganem |
| 6,306,170 B1 * | 10/2001 | Ray ........................ 623/17.11 |
| 6,432,106 B1 * | 8/2002 | Fraser ........................ 606/61 |
| 6,565,571 B1 | 5/2003 | Jackowski |
| 6,613,091 B1 * | 9/2003 | Zdeblick et al. ......... 623/17.16 |
| 6,712,820 B1 | 3/2004 | Orbay |
| 6,740,088 B1 | 5/2004 | Kozak et al. |
| 6,835,206 B1 * | 12/2004 | Jackson .................... 623/17.11 |
| 2004/0199254 A1 * | 10/2004 | Louis et al. ............. 623/17.11 |

FOREIGN PATENT DOCUMENTS

| | | |
|---|---|---|
| FR | 2742653 | 12/1995 |
| WO | WO 97/20526 | 6/1997 |
| WO | WO 99/63914 | 12/1999 |

* cited by examiner

ANTERIOR LUMBAR INTERBODY FUSION CAGE WITH LOCKING PLATE

FIELD OF THE INVENTION

The present invention relates to medical devices, and more particularly to an implantable structure for promoting fusion of adjacent vertebral bodies.

BACKGROUND OF THE INVENTION

Advancing age, as well as injury, can lead to changes in the bones, disks, joints, and ligaments of the spine producing pain from nerve root compression. Under certain circumstances, alleviation of pain can be provided by performing a spinal fusion. This is a procedure that involves joining two or more adjacent vertebrae with a bone fixation device so that they no longer are able to move relative to each other. For a number of known reasons, bone fixation devices are useful for promoting proper healing of injured or damaged vertebral bone segments caused by trauma, tumor growth, or degenerative disc disease. The external fixation devices immobilize the injured bone segments to ensure the proper growth of new osseous tissue between the damaged segments. These types of external bone fixation devices often include internal bracing and instrumentation to stabilize the spinal column to facilitate the efficient healing of the damaged area without deformity or instability, while minimizing any immobilization and post-operative care of the patient.

One such device is bone fixation plate that is used to immobilize adjacent skeletal parts such as bones. Typically, the fixation plate is a rigid metal or polymeric plate positioned to span bones or bone segments that require immobilization with respect to one another. The plate is fastened to the respective bones, usually with bone screws, so that the plate remains in contact with the bones and fixes them in a desired position. Bone plates can be useful in providing the mechanical support necessary to keep vertebral bodies in proper position and bridge a weakened or diseased area such as when a disc, vertebral body or fragment has been removed.

Such plates have been used to immobilize a variety of bones, including vertebral bodies of the spine. These bone plate systems usually include a rigid bone plate having a plurality of screw openings. The openings are either holes or slots to allow for freedom of screw movement. The bone plate is placed against the damaged vertebral bodies and bone screws are used to secure the bone plate to the spine and optionally to a prosthetic implant positioned between the adjacent vertebrae.

While several types of bone fixation plates exists, there remains a need for an improved locking plate and system.

SUMMARY OF THE INVENTION

In general, the present invention provides a spinal fixation assembly including a fusion cage with posterior, anterior, superior, and inferior faces, and a plate having at least one aperture for receiving a bone screw and being configuration to slidably mate to the fusion cage. In one embodiment, the plate includes a mating element for engaging the cage in an anterior-posterior direction. The mating element can have a variety of configurations, but it preferably takes the form of opposed first and second arms that are adapted to engage the superior and inferior faces of the fusion cage. The first and second arms can be flexible, and preferably extend from the plate and are adapted to seat on the superior and inferior faces of the fusion cage. The superior and inferior faces of the fusion cage can each include an arm-seating recess formed therein for receiving the first and second arms on the plate. These recesses allow the arms to sit flush with the superior and inferior faces when disposed within the arm-seating recesses. In an exemplary embodiment, the first and second arms are adapted to mate with the arm-receiving recesses formed on the fusion cage with an interference fit to temporarily secure the plate to the fusion cage.

In another embodiment, the anterior face of the fusion cage can include at least one bore formed therein, and the mating element can be at least one arm that is adapted to extend into the bore in the fusion cage to mate the plate to the fusion cage. In a preferred embodiment, the anterior face of the fusion cage includes a superior bore and an inferior bore formed therein, and the mating element comprises opposed first and second arms that are adapted to extend into the superior and inferior bores in the fusion cage to mate the plate to the fusion cage.

In another embodiment, the fusion cage includes an intermediate plane that separates the inferior face from the superior face to define an inferior side and a superior side, and the plate includes at least one inferior aperture on the inferior side of the fusion cage and at least one superior aperture on the superior side of the fusion cage. Each aperture in the plate can have a first end having an opening, a second, opposed end, and a sidewall extending therebetween that defines an inner lumen. The first end of each aperture preferably is a generally spherical recess formed in the plate for rotatably seating a head of a bone screw. A split bushing is preferably disposed within each aperture in the plate. Each aperture can optionally include an anti-rotation mechanism effective to prevent each split bushing from rotating within the aperture. The apertures and the split bushings can have a variety of configurations. In one embodiment, the sidewall of each aperture can be concave and each split bushing can include a convex outer surface. Each split bushing can also optionally include a shoulder formed therein that abuts a corresponding shoulder formed within each aperture. In another embodiment, each split bushing can include an inner surface having threads formed thereon that are adapted to mate with corresponding threads formed on a bone screw.

In other aspects, the inferior and superior apertures are disposed in inferior and superior tabs. The tabs are preferably angled with respect to the fusion cage in a direction anterior to the anterior face of the fusion cage. In an exemplary embodiment, each tab extends in a plane, and each aperture defines a central axis that extends through the aperture at an angle with respect to the plane of the tab in which the aperture is disposed.

BRIEF DESCRIPTION OF THE DRAWINGS

The invention will be more fully understood from the following detailed description taken in conjunction with the accompanying drawings, in which.

DETAILED DESCRIPTION OF THE DRAWINGS

In general, the present invention provides a spinal fixation assembly including a fusion cage with posterior, anterior, superior, and inferior faces, and a plate having at least one aperture for receiving a bone screw and having a mating element adapted to slidably engage and mate to the anterior face of the fusion cage. The cage is adapted to be positioned between adjacent vertebrae, and the plate is effective to mate to the cage and to receive one or more bone screws to fasten the plate and secure the fusion cage to the adjacent vertebrae.

Figure 1:
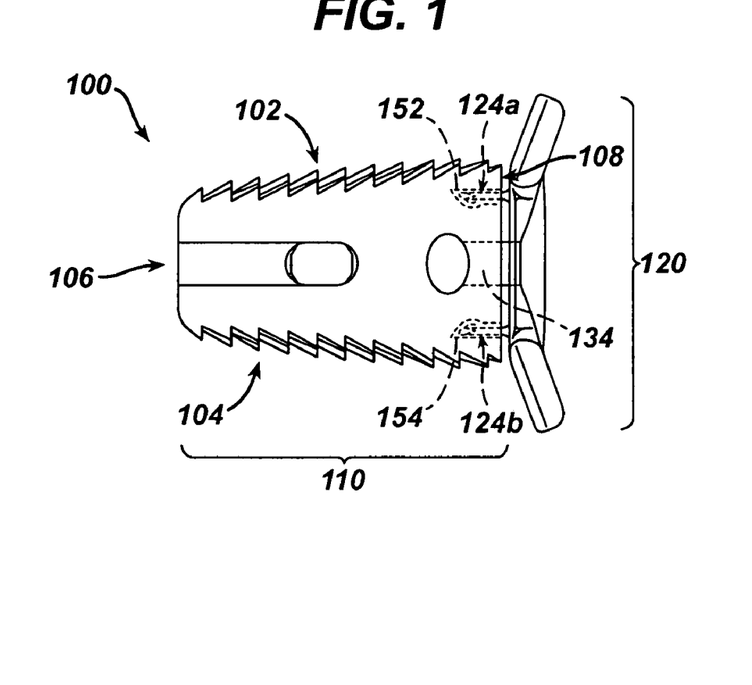
FIG. 1 is a side view of a spinal fixation assembly having a plate and a fusion cage.

As shown in FIG. 1, the assembly 100 generally includes a fusion cage 110 and a plate 120 which slidably mates to the cage 110 in a superior/inferior direction. The fusion cage 110 includes superior 102, inferior 104, posterior 106 and anterior sides 108, and the plate 120 includes at least one aperture 122a–d (shown in FIG. 2) for receiving a bone screw. The plate 120 further includes a mating element 124a, 124b adapted to slidably engage and mate to the anterior face 108 of the fusion cage 110. A person having ordinary skill in the art will appreciate that the plate 120 can mate to any side of the cage 110.

Figure 2:
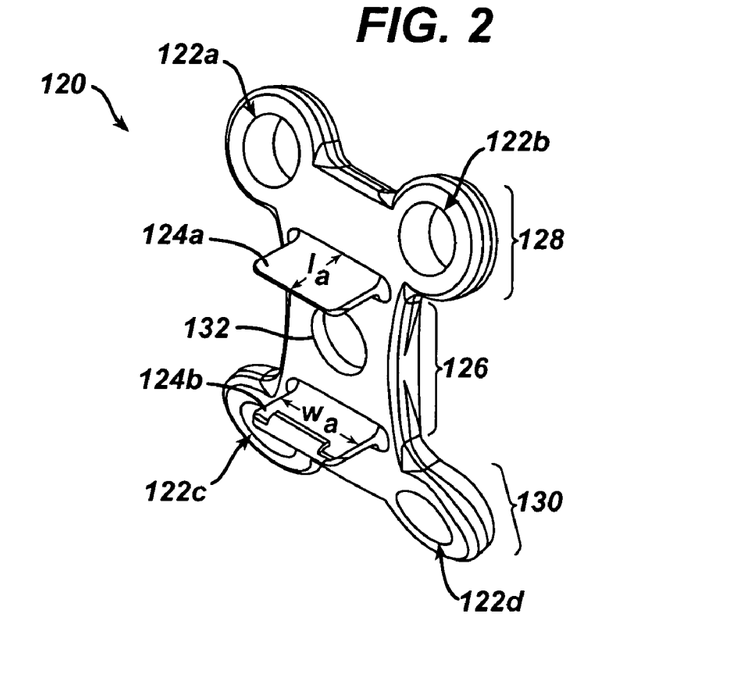
FIG. 2 is a perspective view of the plate shown in FIG. 1.

The plate 120, which is shown in more detail in FIG. 2, can have a variety of configurations. As shown, the plate 120 has a generally planar shape and includes a mid-portion 126 that is positioned between superior and inferior portions 128, 130, also referred to herein as tabs. When the plate 120 is mated to the fusion cage 110, the superior portion 128 of the plate 120 is adapted to extend beyond the superior surface 102 of the fusion cage 110, and the inferior portion 130 of the plate 120 is adapted to extend beyond the inferior surface 104 of the fusion cage 110. While the plate 120 is preferably substantially planar, the mid-portion 126 of the plate 120 can be curved to contour the shape of the anterior face 108 of the fusion cage 110. Moreover, the superior and inferior portions 128, 130 of the plate 120 can extend at an angle with respect to the mid-portion 126 of the plate 120, as shown.

Figure 3:
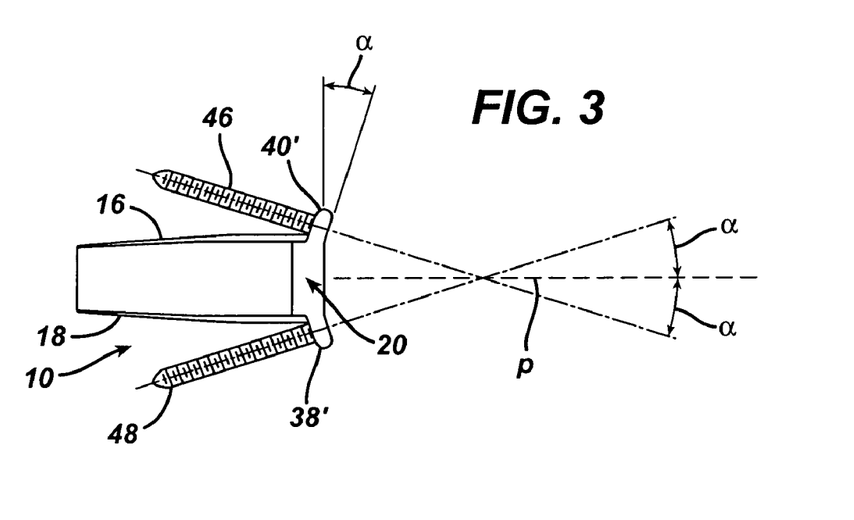
FIG. 3 is a side view of another embodiment of a fusion cage with bone screws.

FIG. 3 illustrates one embodiment of an implant 10 having a plate 20 mated thereto with bone screws 46 and 48, each having a head and a shank, disposed through the holes in tabs 40' and 38'. Tabs 38' and 40' are shown angled with respect to the remainder of the plate 20 so that screws 46 and 48 are angled with respect to the medial plane "P" of the body 10. The angle formed by the tab(s) and plate, as well as by the screw(s) and medial plane, is designated as "α" and is determined by a particular situation and a patient's anatomy. Although the angle "α" can range from 15° to 60°, for most applications the angle "α" is about 20°. However, in other embodiments, the tabs are flexible or readily bent with respect to the remainder of the plate 20. Also shown in FIG. 3 are other advantageous features of the fusion cage, such as flat to slightly convex inferior and superior face surfaces 18 and 16, respectively, and a slightly tapered (about 10°) or wedge profile, wherein the body 10 is thicker at the anterior face 12 than at the posterior face 14.

Referring back to FIG. 2, each of the superior and inferior portions 128, 130 of the plate 120 further include at least one aperture 122a–d formed therein for receiving a bone screw to secure the plate 120 to a vertebra. As shown, the superior and inferior portions 128, 130 of the plate 120 each include two apertures 122a, 122b, 122c, 122d formed therein. The apertures 122a–d will be discussed in more detail with respect to FIGS. 6–10.

The mid-portion 126 of the plate 120 can also include a central aperture 132 formed therein. The central aperture 132 is positioned such that it is aligned with a central bore 134 (FIG. 1) formed in the fusion cage 110 when the plate 120 is mated to the cage 110. The central aperture 132 and bore 134 are effective to receive an insertion tool and/or a fastening element, such as a screw, effective to mate the plate 120 to the fusion cage 110. In one embodiment (not shown), the fastening element can be fixedly, but rotatably disposed within the central aperture 132 of the plate 120, and it can be adapted to snap into the central bore 134 in the fusion cage 110. The fastening element can further be adapted to engage the fusion cage 110 upon rotation thereof. A person having ordinary skill in the art will appreciate that a variety of techniques can be used to mate the plate 120 to the fusion cage 110.

Figure 4:
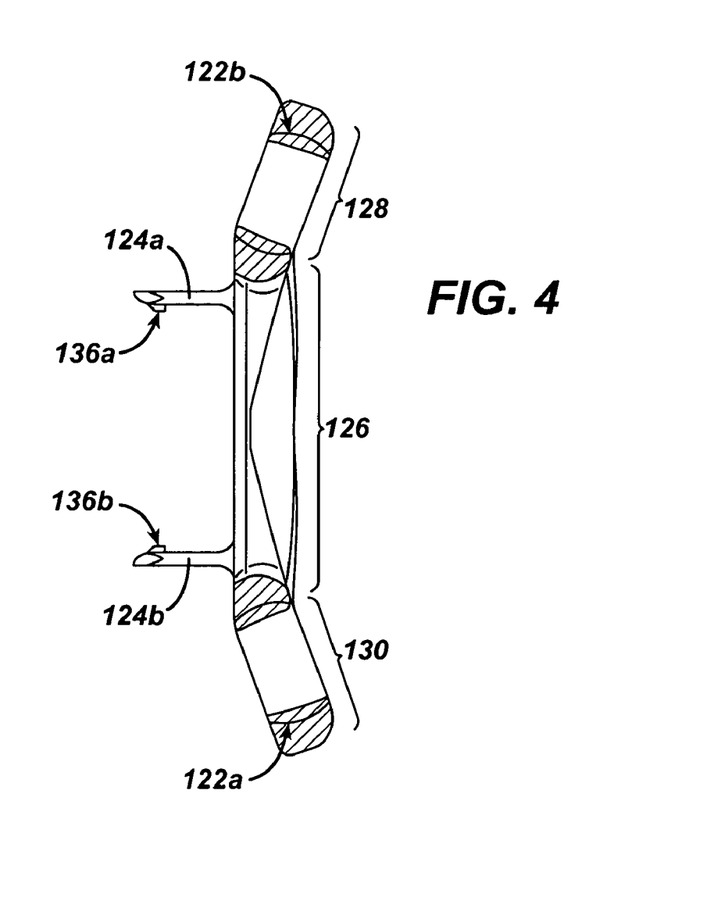
FIG. 4 is side view of the plate shown in FIG. 1.

Referring now to FIGS. 2 and 4, the plate 120 further includes a mating element 124a, 124b adapted to slidably engage and mate the plate 120 to the anterior face 108 of the fusion cage 110 in an anterior-posterior direction. While the mating element 124a, 124b can have a variety of configurations, FIGS. 2 and 4 illustrate first and second opposed arms 124a, 124b that extend outward from the plate 120 in a direction substantially perpendicular to the substantially planar surface of the plate 120. The arms 124a, 124b can be positioned anywhere on the plate 120, but preferably the first arm 124a is positioned just superior to the mid-portion 126 of the plate 120 between the central aperture 132 and the superior apertures 122a, 122b formed in the superior portion 128 of the plate 120, and the second arm 124b is positioned just distal to the mid-portion 126 of the plate 120 between the central aperture 132 and the inferior apertures 122c, 122d formed in the inferior portion 130 of the plate 120. In other words, the arms 124a, 124b are positioned such that, when the plate 120 is mated to the fusion cage 110, the arms 124a, 124b are configured to engage the superior and inferior faces 102, 104 of the fusion cage 110.

The shape of the arms 124a, 124b can also vary, but preferably each arm 124a, 124b is adapted to contour the shape of the fusion cage 110. By way of non-limiting example, where the fusion cage 110 has domed or convex superior and inferior surfaces 102, 104, the arms 124a, 124b are preferably convex to contour the shape of the fusion cage 110. The size of each arm 124a, 124b can vary as well, but preferably each arm 124a, 124b has a length $l_a$ sufficient to enable the arms 124a, 124b to extend across at least a portion of the superior and inferior surfaces 102, 104 of the fusion cage 110, and a width $w_a$ sufficient to allow the arms 124a, 124b to grasp the fusion cage 110.

Each arm 124a, 124b can have a variety of configurations, but preferably the arms 124a, 124b include an engagement element 136a, 136b effective to engage the superior and inferior faces 102, 104 of the fusion cage 110. The engagement element 136a, 136b preferably provides an interference fit to temporarily secure the plate 120 to the fusion cage 110. While the engagement element 136a, 136b can have a variety of configurations, the engagement element 136a, 136b can be, for example, in the form of at least one protrusion formed on an inner surface of each arm 124a, 124b that is adapted to sit in at least one indentation 138 (shown in FIG. 5) formed in each of the superior and inferior faces 102, 104 of the fusion cage 110. As shown in FIG. 4, the protrusion 136a, 136b on each arm 124a, 124b has a generally elongate shape. The indentation will be discussed in more detail with respect to FIG. 5 below. The arms 124a, 124b can optionally be flexible to allow the arms 124a, 124b to flex outward while sliding the plate 120 onto the fusion cage 110, and to allow the arms 124a, 124b to then return to their original state whereby the protrusions 136a, 136b on the arms 124a, 124b to snap into the indentations 138 (only one indentation is shown in FIG. 5) formed in the superior and inferior faces 102, 104 of the fusion cage 110.

Figure 5:
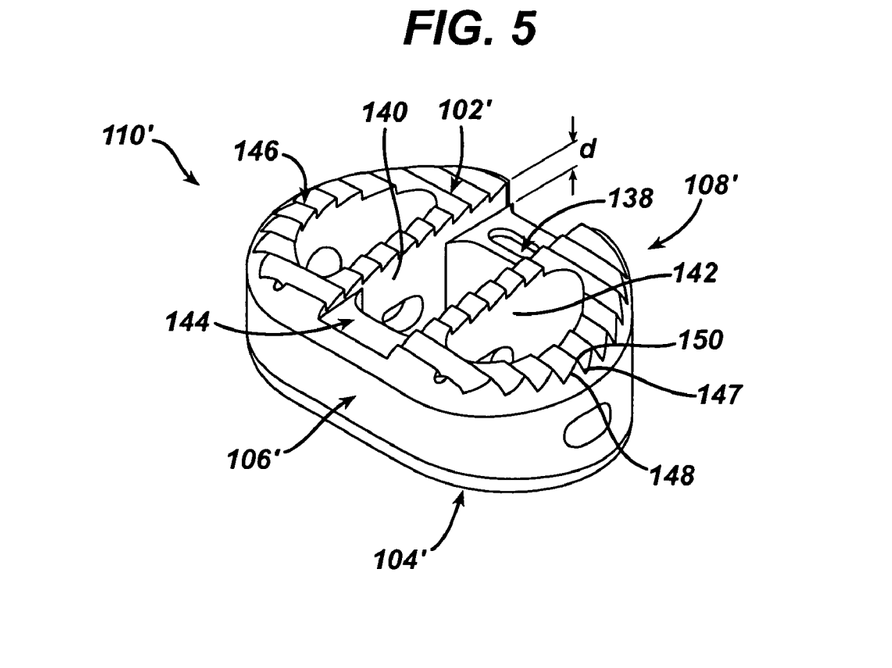
FIG. 5 is a perspective view of the fusion cage shown in FIG. 2.

Referring now to FIG. 5, an exemplary embodiment of a fusion cage 110' is shown in more detail and can have a variety of configurations. The fusion cage 110' includes superior 102', inferior 104', posterior 106', and anterior 108' faces. A central bore (not shown) is formed in the anterior face 102' of the fusion cage 110', and preferably includes threads formed therein for receiving a fastening element, e.g., a screw. The threads are preferably spinal lock threads to provide a secure connection between the plate and the cage. First and second transverse elements 140, 142 can join the posterior face 106' to the anterior face 108', and a guide path 144 for receiving an insertion tool can extend across the superior and inferior faces 102', 104' between the posterior and anterior faces 106', 108'.

Fusion cage 110' further includes an arm-seating recess formed in each of the superior and inferior surfaces 102', 104' for receiving the arms 124a, 124b formed on the plate 120. The recesses can be formed in the guide path 144, or more preferably the guide path 144 can form arm-seating recesses, as is shown in FIG. 5. Each guide path 144 (only the guide path on the superior surface 102' is shown), or arm-seating recess, preferably has a depth d sufficient to receive the corresponding arm 124a, 124b formed on the plate 120 such that, when the plate 120 is mated to the fusion cage 110', the arms 124a, 124b are flush with the superior and inferior surfaces 102', 104' of the fusion cage 110'. This is particularly advantageous in that it allows the fusion cage 110' to be positioned between adjacent vertebrae prior to inserting the arms 124a, 124b into the arm-seating recesses 144 to attach the plate 120 to the fusion cage 110'. Each of the arm-seating recesses 144 further preferably includes at least one indentation 138 formed therein for receiving the protrusion 136a, 136b formed on the inner surface of each arm 124a, 124b. As shown, the indentation 138 is in the form of an elongate groove that is adapted to receive and seat the protrusion 136a, 136b formed on each arm 124a, 124b. A person having ordinary skill in the art will appreciate that the arms 124a, 124b can merely slid into and seat within the recess 144 formed in the fusion cage 110', and that they do not need to engage the fusion cage 110'. An engagement mechanism is merely preferred to allow the plate 120 to be at least temporarily secured to the fusion cage 110' during implantation.

The fusion cage 110' can optionally include a number of bone engaging surface features 146 formed on the superior and inferior surfaces 102', 104' to facilitate the secure mounting of the cage 110' between adjacent vertebrae. The bone engaging surface features 146 can be present on the entire surface area of the superior and inferior surfaces 102', 104', or optionally, selected regions of the superior and inferior surfaces 102', 104' can be free of surfaces features 146. The bone engaging surface features 146 can have a variety of shapes, but are preferably in the form of wedge-shaped ridges that extend is a direction transverse to the posterior 106' and anterior 108' faces of the fusion cage 110'. Each bone engaging surface feature 146 includes a posterior side wall 148 and an anterior side wall 149, which meet at a peak 150. The side walls 148, 149 of each surface feature 146 can be angled or sloped to facilitate insertion of the cage 110' between adjacent vertebrae and to assist in preventing the fusion cage 110' from becoming dislodged. The size of the surface features 146 can also vary but preferably the surface features 146 have a size sufficient to cause each surface feature 146 to engage and penetrate the adjacent vertebrae. It will be understood that while ridges 146 have been shown in a preferred embodiment, it is contemplated that there are a variety of structures which could provide a surface for effective engagement with the vertebral bodies to limit expulsion from the disc space.

In yet another embodiment of a spinal fixation assembly, the arms 124a, 124b on the plate 120 can be adapted to extend into opposed superior and inferior bores 152, 154, rather than recesses 144, formed in the fusion cage 110. Referring back to FIG. 1, the arms 124a, 124b can merely slide into the bores 152, 154 that extend into the fusion cage 110 to provide an alignment mechanism between the cage 110 and the plate 120. The bores 152, 154 can optionally be adapted to receive the engagement mechanism 136a, 136b formed on each arm 124a, 124b to at least temporarily secure the arms 124a, 124b within the bores 152, 154. By way of non-limiting example, the arms 124a, 124b and the bores 152, 154 can each be tapered to provide an interference fit between the arms 124a, 124b and the bores 152, 154. Alternatively, the arms 124a, 124b can include a press-fit pin that depresses upon insertion of the arms 124a, 124b into the bores 152, 154, and then once each arm 124a, 124b is fully inserted into the bore 152, 154, returns to its originally state whereby the pins extending into corresponding indentations formed within the bores 152, 154. A person having ordinary skill in the art will appreciate that a variety of mechanisms can be used to secure the arms 124a, 124b of the plate 120 within the bores 152, 154 formed in the fusion cage 110.

The present invention also provides a variety of configurations for securing the plate 120 to adjacent vertebrae. As previously stated, the plate 120 includes superior and inferior portions or tabs 128, 130 having at least one aperture 122a–d formed therein for receiving a bone screw. FIGS. 6–10 illustrate embodiments of different apertures for use with a plate 120 according to the present invention. The apertures are adapted to provide a more secure connection between the plate 120 and a vertebrae.

Figure 6:
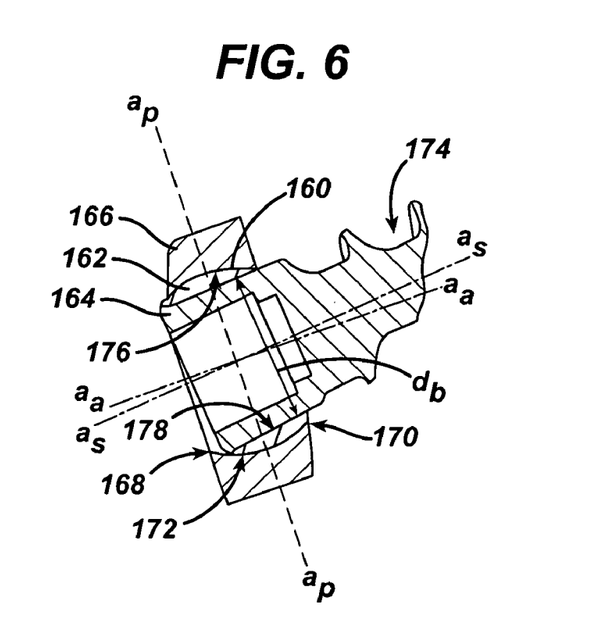
FIG. 6 is a cut-away view of an aperture, split bushing, and bone screw according to the present invention.

FIG. 6 illustrates one embodiment of an aperture 160 formed in a tab 166 of a plate and having a split bushing 162 disposed therein. A bone screw 174 is disposed through the aperture 160 and the split bushing 162. The aperture 160 includes a first end 168, a second end 170, and a sidewall 172 extending therebetween. The first end 168 is preferably adapted to receive a bone screw 174, or similar type of fixation element, and to seat the head 164 of the bone screw 174 therein. The aperture 160 can extend through the tab 166 in the plate along a central axis $a_a$ that is substantially perpendicular to a central plane $a_p$ of the tab 166, or alternatively the central axis $a_a$ of the aperture 160 can be offset from, or disposed at an angle with respect to, the plane $a_p$ of the tab 166. The sidewall 172 of the aperture 160 can also vary and can be either substantially planar along the length thereof between the first and second ends 168, 170 of the aperture 160, or the sidewall 172 can be curved or can extend at an angle. As shown in FIG. 6, the sidewall 172 has a substantially concave shape to receive the split bushing 162.

The split bushing 162 is disposed within the aperture 160 and has a generally cylindrical shape with a gap (not shown) formed therein to allow the bushing 162 to be expanded. The split bushing 162 includes an outer surface 176 which can have a shape adapted to conform to the shape of the sidewall 172 of the aperture 160, and an inner surface 178 which is adapted to receive a bone screw 174. By way of non-limiting example, the split bushing 160 can have a convex outer surface 172 to allow the split bushing 162 to sit within the concave sidewall 172 of the aperture 160. The split bushing 162 further includes an inner diameter $d_b$ that can vary between opposed first and second ends 168, 170 of the split bushing 162. Preferably, the diameter $d_b$ of the bushing 162 at the first end 168 is larger than the diameter $d_b$ of the bushing 162 at the second end 170. The tapered diameter allows the bushing 162 to receive a portion of the tapered undersurface of the head 164 of the bone screw 174.

Figure 7:
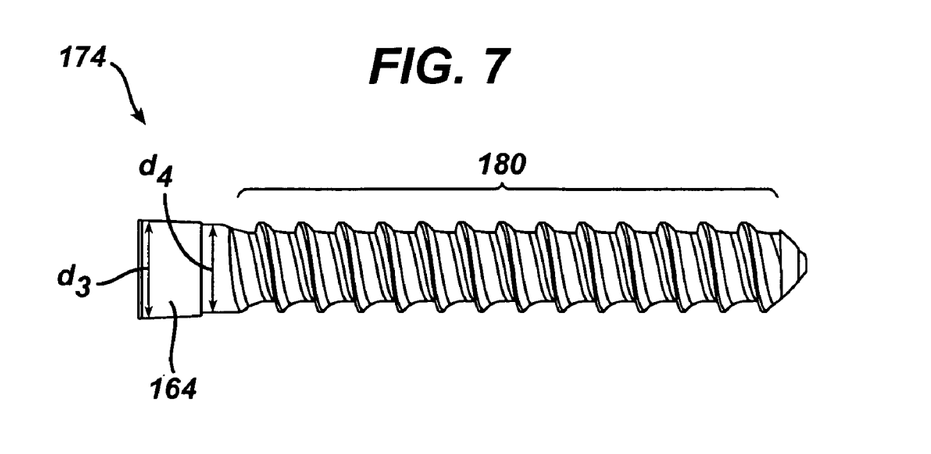
FIG. 7 is a side view of one embodiment of a bone screw according to the present invention.

FIG. 7 illustrates the bone screw 174 in more detail having a tapered head 164 adapted to fit within the split bushing 162 shown in FIG. 6. As shown, the bone screw 174 includes a head 164 and a threaded shank 180. The head 164 is tapered preferably at an angle substantially the same as the angle of the tapered inner diameter $d_b$ of the split bushing 162. In use, upon tightening the bone screw 174, the split bushing 162 expands and provides an interference fit between the bone screw 174 and the aperture 160, thereby creating a rigid lock to secure the plate to a vertebrae. The tapered diameter $d_b$ of the bushing 162 also allows the bone screw 174 to be inserted at variable angles $a_s$ with respect to the central axis $a_a$ of the aperture, as shown in FIG. 6.

Figure 8:
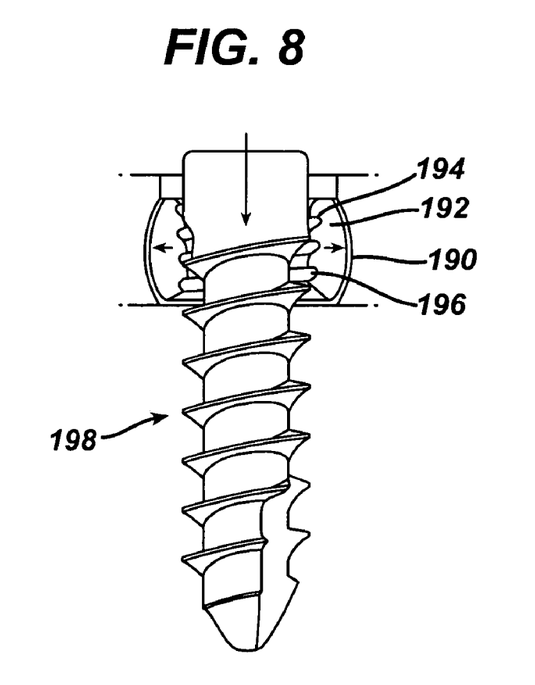
FIG. 8 is a cut-away view of another embodiment of an aperture, split bushing, and bone screw according to the present invention.

FIG. 8 illustrates another embodiment of an aperture 190 having a split bushing 192 disposed therein. In this embodiment, the split bushing 192 includes threads 194 formed on an inner surface thereof to mate with corresponding threads 196 formed on a bone screw 198. The threads 194, 196 are particularly effective to prevent the bone screw 198 from backing out of the aperture 190, and to provide a rigid lock between the screw 198 and the aperture 190 thereby securely mating the plate to a vertebrae. In this embodiment, the aperture 190 preferably includes an anti-rotation mechanism effective to prevent the split bushing 192 from rotating while the screw 198 is threaded therethrough. The anti-rotation mechanism can have a variety of configurations and, by way of non-limiting example, can be a pin or raised protrusion (not shown) disposed within the aperture 190 and adapted to extend into the gap formed in the split bushing 192.

Figure 9:
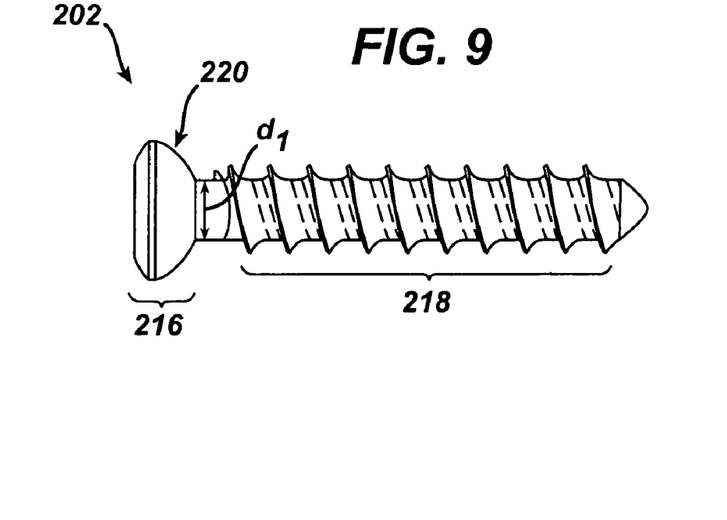
FIG. 9 is a side view of another embodiment of a bone screw according to the present invention.
Figure 10:
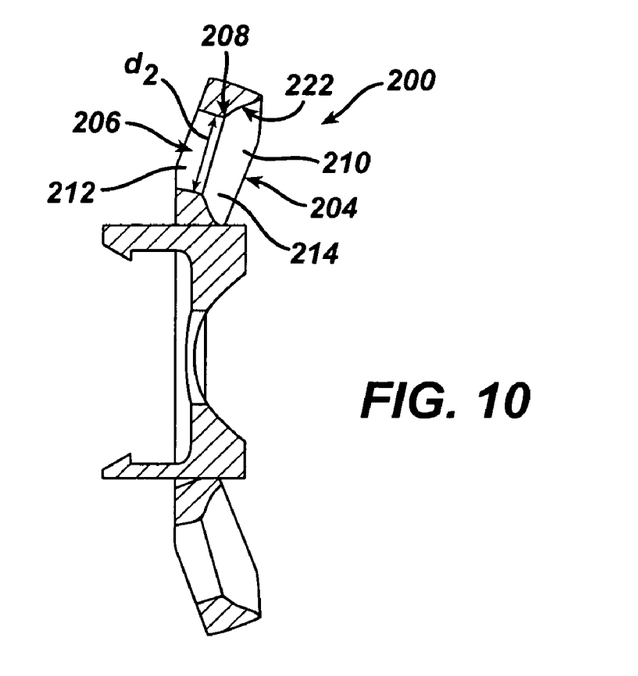
FIG. 10 is a cut-away, side view of a plate having apertures adapted to receive the bone screw shown in FIG. 9.

FIGS. 9–10 illustrate yet another embodiment of an aperture 200 and bone screw 202 for use with the present invention. As shown in FIG. 10, the aperture 200 includes a first end 204, a second end 206, and a sidewall 208 extending therebetween and defining an inner lumen 210. The inner lumen 210 includes a first portion 214 positioned adjacent the first end 204, and a second portion 212 positioned adjacent the second end 206 of the aperture 200. The first portion 214 of the inner lumen 210 has a shape and size adapted to receive the head 216 of a bone screw 202. FIG. 9 illustrates an exemplary embodiment of a bone screw 202 for use with a plate having an aperture 200 as shown in FIG. 10. The bone screw 202 includes a head 216 and a threaded shank 218. The head 216 of the bone screw 202 includes a substantially convex, slightly rounded outer surface 220. The first portion 214 of the inner lumen 210 of the aperture 200 has a concave sidewall 222, e.g., a generally spherical recess, to allow the rounded head 216 of the bone screw 202 to seat therein. The second portion 212 of the inner lumen 210 is substantially cylindrical and has a shape and size adapted to receive the threaded shank 218 of a bone screw 202. Preferably, the second portion 212 of the inner lumen 210 has a diameter $d_2$ greater than a diameter $d_1$ of the shank 218 of the bone screw 202. In use, the first and second portions 214, 212 of the inner lumen 210 allow the bone screw 202 to translate within the aperture 200 such that the screw 202 can be inserted at varying angles. While the aperture 200 does not include a split bushing to provide a rigid connection between the bone screw 202 and the plate, the aperture 200 allows the full exertion of natural biomechanical compression stresses through the vertebral bodies into which the screw 202 is inserted.

Referring back to FIG. 7, in yet another embodiment, the bone screw 174 can include a shoulder 230 formed thereon that abuts a corresponding shoulder (not shown) formed in an aperture. The shoulder 230 is formed by a difference, or stepped increase, in the diameter $d_3$, $d_4$ of the screw head 164 and in the diameter of the aperture, or in the split bushing if the aperture includes one. In use, the bone screw 174 is inserted through an aperture and once the shoulder 230 on the screw head 164 passes the shoulder 230 in the aperture, or in the split bushing, the shoulders will engage thereby preventing the screw 174 from backing out of the aperture.

The fusion cage and plate of the present invention can be made from a variety of materials. By way of non-limiting example, a carbon fiber composite or other radiolucent material is well suited for fabrication of the body, and titanium or carbon fiber composites are suitable materials for the plate 20.

In use, adjacent vertebrae are distracted, the disc is removed, and the area is prepared using techniques known in the art. Prior to inserting the fusion cage between the adjacent vertebrae, the space bounded by the body of the cage and the transverse elements is preferably filled with autograft, allograft bone, and/or demineralized bone matrix to promote fusion. The fusion cage is then positioned between the vertebrae using a variety of devices. Distractor and spreader devices are known in the art, and are effective for separating adjacent vertebrae, and optionally assisting with insertion of the implant. Typical distractors include two opposed blade members which are inserted between the adjacent vertebrae, and then opened to separate the vertebrae. The fusion cage can then be inserted into the disk space either manually, or using an impacting device, such as a mallet. Once the fusion cage is in position, the plate is mated to the anterior face of the fusion cage by positioning the arms between the superior and inferior surfaces of the fusion cage and the adjacent vertebrae. Where the cage includes arm-receiving recesses, the arms of the plate can be easily slid into the recesses to engage the cage. A center screw can then be inserted through the central aperture in the plate and through the bore in the cage to secure the plate to the cage, and one or more bone screws can be inserted through the superior and inferior apertures in the plate to secure the plate to the adjacent vertebrae.

As should be readily apparent from the preceding description, the present invention provides many advantages. For example, the fusion cage is sufficiently broad and thick so that only a single cage is needed to replace an excised disk. The profile and slightly bowed or convex superior and inferior surfaces of the fusion cage body closely approximate the shape of a natural disk and provide an excellent, stable, load-bearing surface. The plate, when included, ensures that the body will not become dislodged from the spine, yet is readily accessible with an anterior approach. Further, the plate allows bone screws to be deeply embedded into the vertebral bodies without piercing or otherwise damaging the hard, load-bearing, cortical bone. Also, both the plate and the body include features that allow for relatively easy manipulation and insertion with appropriately configured surgical tools.

Of course, one skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal fixation assembly, comprising:
a fusion cage having posterior, anterior, superior, and inferior faces; and
a plate having at least one aperture for receiving a bone screw and having opposed first an second arms that are adapted to slidably receive the fusion cage therebetween such that the opposed first and second arms engage and mate to the superior and inferior faces of the fusion cage in an anterior-posterior direction.

2. The spinal fixation assembly of claim 1, wherein the superior and inferior faces of the fusion cage each include an ann-seating recess formed therein for receiving the first and second arms on the plate.

3. The spinal fixation assembly of claim 2, wherein the arms are flush with the superior and inferior faces when disposed within the arm-seating recesses.

4. A spinal fixation assembly 4, comprising:
a fusion cage having posterior, anterior, superior, and inferior faces, the superior and inferior faces of the fusion cage each including an arm-seating recess formed therein; and
a plate having at least one aperture for receiving a bone screw and having first and second arms adapted to mate with the arm-receiving recesses formed on the fusion cage with an interference fit to temporarily secure the plate to the fusion cage.

5. The spinal fixation assembly of claim 4, wherein at least one of the arm-receiving recess and the first and second arms includes at least one protrusion formed thereon and adapted to seat in at least one indentation formed in the other one of the arm-receiving recesses and the first and second arms.

6. The spinal fixation assembly of claim 4, wherein the first and second arms are flexible.

7. The spinal fixation assembly of claim 1, wherein the anterior face of the fusion cage includes a central bore formed therein, and the plate includes a central aperture extending therethrough and aligned with the central bore, the central aperture and the central bore being adapted to receive a center screw for mating the plate to the fusion cage.

8. The spinal fixation assembly of claim 1, wherein the fusion cage includes an intermediate plane that separates the inferior face from the superior face to define an inferior side and a superior side, and wherein the plate defines at least one inferior aperture on the inferior side of the fusion cage and at least one superior aperture on the superior side of the fusion cage.

9. The spinal fixation assembly of claim 8, wherein each aperture in the plate has a first end and a second, opposed end with a sidewall extending therebetween that defines an inner lumen, the assembly further comprising a split bushing disposed within the inner lumen of each aperture in the plate.

10. The spinal fixation assembly of claim 9, wherein the sidewall of each aperture is concave and wherein each split bushing includes a convex outer surface.

11. The spinal fixation assembly of claim 10, wherein each split bushing includes a tapered inner lumen.

12. The spinal fixation assembly of claim 9, wherein each split bushing includes a shoulder formed therein that abuts a corresponding shoulder formed within each aperture.

13. The spinal fixation assembly of claim 9, wherein each split bushing includes an inner surface having threads formed thereon that are adapted to mate with corresponding threads formed on a bone screw.

14. The spinal fixation assembly of claim 9, wherein each aperture includes an anti-rotation mechanism effective to prevent each split bushing from rotating within the aperture.

15. The spinal fixation assembly of claim 14, wherein the anti-rotation mechanism comprises a raised protrusion adapted to be positioned in a split formed in the split bushing.

16. The spinal fixation assembly of claim 9, wherein the first end of each aperture has a generally spherical recess formed therein for rotatably seating a head of a bone screw.

17. The spinal fixation assembly of claim 8, wherein the inferior and superior apertures are disposed in inferior and superior tabs.

18. The spinal fixation assembly of claim 17, wherein the tabs are angled with respect to the fusion cage in a direction anterior to the anterior face of the fusion cage.

19. The spinal fixation assembly of claim 17, wherein each tab extends in a plane, and wherein each aperture defines a central axis that extends through the aperture at an angle with respect to the plane of the tab in which the aperture is disposed.

20. The spinal fixation assembly of claim 19, wherein the angle of the central axis of each aperture is in the range of about 0° to 45°.

21. The spinal fixation assembly of claim 1, further including a plurality of surface features extending outward from the fusion cage on one of the superior face and the anterior face.

22. The spinal fixation assembly of claim 21, wherein the surface features are selected from the group consisting of fins, ridges, and teeth.

23. A spinal fixation assembly, comprising:
a fusion cage having posterior, anterior, superior, and inferior faces; and
a plate having at least one aperture for receiving a bone screw and having opposed arms for slidably receiving the fusion cage therebetween and for mating and engaging the plate to the anterior face of the fusion cage in an anterior-posterior direction.

24. The spinal fixation assembly of claim 23, wherein the superior and inferior faces at fusion cage each include a recess for receiving an arm.

* * * * *